(12) United States Patent
van den Boogard et al.

(10) Patent No.: US 8,268,059 B2
(45) Date of Patent: Sep. 18, 2012

(54) WASTE GAS SYSTEM FOR BIOREACTORS

(75) Inventors: Juergen van den Boogard, Dransfeld (DE); Gerid Hellwig, Goettingen (DE); Jens Ludwig, Juehnde (DE); Oscar-Werner Reif, Hannover (DE); Stefan Weisshaar, Goettingen (DE)

(73) Assignee: Sartorius Stedim Biotech GmbH (DE)

( * ) Notice: Subject to any disclaimer, the term of this patent is extended or adjusted under 35 U.S.C. 154(b) by 177 days.

(21) Appl. No.: 12/653,506

(22) Filed: Dec. 15, 2009

(65) Prior Publication Data
US 2010/0170400 A1    Jul. 8, 2010

(30) Foreign Application Priority Data
Jan. 7, 2009 (DE) .......................... 10 2009 003 972

(51) Int. Cl.
*B01D 50/00* (2006.01)
(52) U.S. Cl. .......... 96/221; 95/288; 55/467.1; 55/490.1; 55/490.2
(58) Field of Classification Search .................... 96/221; 95/288, 289; 55/467.1, 490.1, 490.2
See application file for complete search history.

(56) References Cited

U.S. PATENT DOCUMENTS
5,443,985 A     8/1995  Lu et al.
7,582,140 B2 *  9/2009  Silva et al. ....................... 95/273

FOREIGN PATENT DOCUMENTS
AT    396 979 B      5/1993
CH       244453      9/1946
DE     1 601 144    11/1970
EP    0 915 965 B1   1/2003

OTHER PUBLICATIONS

BioFlo 310—German Company Brochure B-4018 10P42006, New Brunswick Scientific GmbH—Oct. 2006 (German lanugage).
BioFlo 310—German Company Brochure B-4018 10P42006, New Brunswick Scientific GmbH—Oct. 2006 (English language translation).

* cited by examiner

*Primary Examiner* — Robert A Hopkins
(74) *Attorney, Agent, or Firm* — Gerald E. Hespos; Michael J. Porco

(57) ABSTRACT

The invention relates to a waste gas system for bioreactors having a hydrophobic sterile filter, arranged at the end, and a heat exchanger which protects the sterile filter against blocking by liquid media. The gas outflow duct for discharging waste gas from a bioreactor vessel is divided in a cooling zone of the heat exchanger into a multiplicity of subducts and is extended in a heating zone of the heat exchanger to a calming zone. Due to the multiplicity of subducts, a considerably larger surface area for the removal of heat from the waste gas is available, with the result that in the case of laminar flow of the waste gas through the subducts a high effectiveness of the separation of liquids from the waste gas can be achieved. In the heating zone, the waste gas can heat up again due to the reduced flow rate until it reaches the hydrophobic sterile filter by way of taking up heat from the surroundings to a such a degree that the relative vapor contents are below 100% and separation of liquids from residual vapors at or in the hydrophobic sterile filter is precluded.

22 Claims, 1 Drawing Sheet

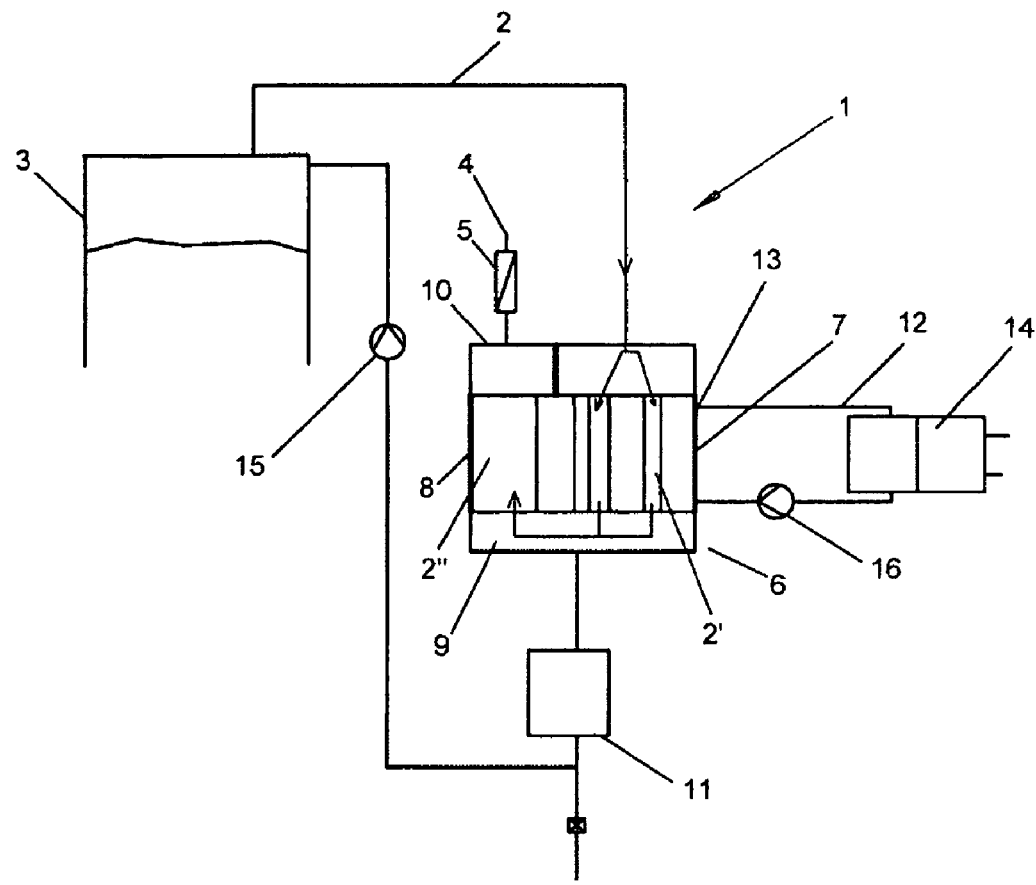

WASTE GAS SYSTEM FOR BIOREACTORS

BACKGROUND OF THE INVENTION

1. Field of the Invention

The invention relates to a waste gas system for bioreactors with a hydrophobic sterile filter, arranged at the end, and a heat exchanger which protects the sterile filter in a particular manner against blocking by liquid media.

2. Description of the Related Art

When gas is introduced into a bioreactor, it takes up liquid vapors as it flows through a liquid medium, which liquid vapors would be entrained out in an undesired manner during uncontrolled exit from the bioreactor. The same effect would occur in biotechnological processes, where gases are formed as metabolic products and removed from the bioreactor. In order to avoid contamination, the opening in a bioreactor is usually provided with a sterile filter for gas removal purposes. According to the unpublished patent application DE 10 2008 025 968.3 by the applicant, the use of a condenser located in the gas outflow duct under turbulent flow of the waste gas is intended to prevent the sterile filter from being blocked by condensing liquids and the waste gases from entraining out some of the liquid culture medium. It is a disadvantage that owing to the turbulent flow a pronounced reduction in pressure occurs in the gas outflow duct. As a result, the bioreactors should be operated at relatively high pressures in the gas chamber, which is undesired for some reaction processes and in particular for such bioreactors composed of flexible plastic bags due to the risk of the occurrence of leakages. There is also the risk that liquid droplets will be entrained up to the sterile filter or will be precipitated in it and block it.

U.S. Pat. No. 5,443,985 A discloses a bioreactor having a vessel, which has at its upper end, in the vertical direction, a gas outflow duct for discharging gas. A water-cooled condenser is arranged between the vessel and a waste gas filter. The inside wall surrounding the gas outflow duct forms the condensation surface of the condenser. It is a disadvantage in this case that, if the gas throughput is too great, at least partial blocking of the waste air filter by condensate occurs. This is not even prevented if a relatively long condenser is used for cooling the waste gases. If the waste gas filter were to become too blocked, the introduction of gas and thus the culture process would have to be stopped.

U.S. Pat. No. 6,133,021 A likewise discloses a bioreactor having a water-cooled condenser in the gas outflow duct, which has the disadvantage that without a filter the waste gas escapes into the surroundings and the bioreactor is not protected by way of a sterile barrier.

Furthermore, DD 260 837 A3 discloses a fermenter having a vessel having a gas outflow duct for discharging gas. The opening of the gas outflow duct toward the surroundings is provided with a waste air filter (not described in more detail). The waste air flows either through a waste air condenser and the condensate which has formed drops back into the fermenter or it flows through a waste air cooler and the condensate collects in a condensate vessel. This waste gas system also has the above-mentioned disadvantages and is not suitable for a bioreactor having a hydrophobic sterile filter as a waste gas filter.

It is therefore an object of the present invention to propose an effective waste gas system for bioreactors which ensures a high degree of reliability during operation of the bioreactor.

SUMMARY OF THE INVENTION

The object is achieved by way of a waste gas system for bioreactors, at least comprising at least one gas outflow duct for discharging waste gas from a bioreactor vessel, wherein a hydrophobic sterile filter is arranged upstream of the opening of the at least one gas outflow duct toward the surroundings with a heat exchanger located upstream thereof. Here, the at least one gas outflow duct is divided in at least one cooling zone of the heat exchanger into a multiplicity of subducts, and the at least one gas outflow duct is extended in at least one heating zone of the heat exchanger to a calming zone for the waste gas. Due to the division of the gas outflow duct into a multiplicity of subducts in the cooling zone of the heat exchanger, a considerably larger surface area for the removal of heat from the waste gas via the subducts is available, with the result that even in the case of laminar flow of the waste gas through the subducts a high effectiveness of the separation of liquids from the waste gas can be achieved. In the heating zone, which follows for the waste gas and in which the gas outflow duct extends to a calming zone for the waste gas, the waste gas can heat up again due to the reduced flow rate until it reaches the hydrophobic sterile filter by way of taking up heat from the surroundings to such a degree that the relative vapor contents are below 100% and separation of liquids from residual vapors at or in the hydrophobic sterile filter is precluded. As a result, the hydrophobic sterile filter is reliably protected against becoming blocked by liquids.

In order to realize a compact, space-saving design, the series-connected cooling and heating zones of the heat exchanger are preferably arranged in a mutually parallel fashion or at an angle of less than 180° and larger than 0° with respect to one another.

Advantageously, the cooling and the heating zones of the heat exchanger are here connected in a communicating fashion via a base element and, in a preferred embodiment, additionally held together via a head element in order to increase stability. In one preferred embodiment of the invention, the cooling and the heating zones of the heat exchanger are arranged such that they are spaced apart from each other. At least the area of contact between them should be as small as possible. This has the advantage that between them hardly any heat is transferred and the at least one heating zone can readily absorb heat from the surroundings without being adversely affected by the at least one cooling zone. In one advantageous embodiment of the invention, at least the cooling zones of the heat exchanger are connected in a communicating fashion to a condensate collection vessel, which is arranged underneath it, via the base element. An even more compact design is achieved by designing the base element as part of the condensate collection vessel. This enables the arrangement of the waste gas system for example on the side of or underneath the bioreactor vessel. The space above a bioreactor vessel is frequently needed for fittings, such as supply lines and stirrer connectors. It has also proven expedient if the condensate collection vessel is connected to the bioreactor vessel and/or additionally to the at least one heating zone of the heat exchanger, for example via the base element. As a result, condensate which is entrained into the heating zone can drip into the condensate collection vessel. It is possible for the condensate to be recycled, defined as a function of the reaction conditions, from the condensate collection vessel into the bioreactor vessel via valves or pumps, in particular metering pumps. In one embodiment of the invention, the pump is preferably designed as a flexible-tube pump (peristaltic pump). The advantage is that only the flexible tube has media contact and, after a single use, can be discarded in single use systems (disposable systems). The flexible-tube pump, on the other hand, is reusable.

In a further advantageous embodiment of the invention, the waste gas flows, after the cooling zone, through a condensate separator package which is integrated for example in the base element of the heat exchanger. This condensate separator package can be composed of a highly porous non-woven or of fill bodies (e.g. of Raschig rings) which have a large surface area while at the same time having a very low flow resistance. The non-wovens or fill bodies can, for example, be enclosed in a flexible tube in which the condensate can be received. The flexible tube can be located underneath the base element and connects the cooling zone and the heating zone, with the base element not allowing any direct waste gas flow from the cooling zone into the heating zone. These variants described above lead to a further more compact design of the waste gas system. The condensate separator package can be connected to the condensate separator vessel or directly to a pump.

In dependence on the dew point of the liquid vapors in the waste gas, the multiplicity of subducts is surrounded by a cooling medium which is appropriately temperature-controlled. The temperature of the cooling medium should be less than +30° C. Preferred is a range between +10 and −10° C., particularly preferred is a range between +2 and +8° C. In one variant of the invention, at least one Peltier element is introduced for cooling directly into the cooling medium, preferably in the region of the cooling zone. This variant permits further compacting of the waste gas system. However, an embodiment in which heat can be removed from the cooling medium in a circuit has also proven itself. Thus, the circuit is connected for example to a heat pump for the removal of the heat. Peltier elements or thermostats can be used as heat pumps. Optimum cooling of the waste gases is achieved when the ratio of the cross section which is free for the waste gases in the multiplicity of subducts to the free cross section for the cooling medium in the cooling zone is in the range of 5:100 to 75:100, preferably in the range of 10:100 to 50:100.

In the interest of a high reliability and compactness of the waste gas system, in another embodiment of the invention, the sterile filter is designed in the form of a hydrophobic sterile filter and integrated in the exit of the heating zone of the heat exchanger.

Particularly advantageous is a waste gas system according to the invention which is made of plastic. Such a waste gas system can be preassembled together with the bioreactor, but at least already sterilized with the bioreactor vessel by the manufacturer and supplied to the user as a sterile single-use unit. The advantage is of particular importance in bioreactor vessels made of flexible plastics, that is to say when the waste gas system is operable with a bioreactor vessel made of flexible plastic. Such combinations can be reliably sterilized by irradiation, with the irradiation preferably being carried out by way of ionizing irradiation, by way of gamma or electron rays.

For embodiments of the waste gas system according to the invention made of plastic, the multiplicity of subducts in the cooling zone of the heat exchanger is preferably composed of plastics such as polyurethane, silicone or polyalkylene. Particularly preferred is an embodiment in which the subducts are present in the form of flexible tubes. In order that an acceptable heat transfer from the waste gases to the cooling medium can be realized, a wall thickness of the subducts or of the flexible tubes of less than 2 mm is preferred, with a wall thickness of less than 0.6 mm being especially preferred and of less than 0.2 mm being even more preferred.

The lowest pressure losses and efficient condensate formation occur by way of the waste gas system according to the invention if the waste gas during flowing through the multiplicity of subducts has a laminar flow. The laminar flow can be adjusted by way of the number, length and diameter of the subducts in the cooling phase, by way of the diameter and the length of the heating zone and the gas permeability of the hydrophobic sterile filter, which is arranged at the end, as a function of the gas pressure in the bioreactor vessel. In order to approach a maximization in the operation of the waste gas system according to the invention, the flow rate of the waste gas in the subducts of the cooling zone should be at least 0.1 m/s, preferably more than 5 m/s, while maintaining a flow rate of the waste gas in the heating zone of less than 2 m/s, preferably less than 0.05 m/s.

BRIEF DESCRIPTION OF THE DRAWING

The invention will now be explained in more detail using a FIGURE and an exemplary embodiment. Here, the FIGURE shows schematically an embodiment according to the invention of the waste gas system with a bioreactor vessel.

DETAILED DESCRIPTION OF THE PREFERRED EMBODIMENT

The waste gas system 1 is connected, via a gas outflow duct 2, to the gas cushion of a bioreactor vessel 3 for discharging waste gas from the bioreactor vessel 3. Arranged upstream of the opening 4 of the gas outflow duct 2 toward the surroundings is a hydrophobic sterile filter 5 with a heat exchanger 6 located upstream thereof. In this case, the gas outflow duct 2 is divided in a cooling zone 7 of the heat exchanger into a multiplicity of subducts 2', with only two subducts being schematically shown in the FIGURE. In a heating zone 8 of the heat exchanger 6, the gas outflow duct 2 is extended to a calming zone for the waste gas. The cooling and heating zones 7, 8 are held by a base element 9 and a head element 10 and are arranged such that they are spaced apart from each other. Here, the cooling and heating zones 7, 8 are interconnected in a communicating fashion only via the base element 9, while they are separate in the head element 10. In the illustrated embodiment of the FIGURE, a condensate collection vessel 11 is located underneath the base element 9 of the heat exchanger 6, which condensate collection vessel 11 receives the liquid which precipitates from the waste gas vapors in the cooling zone 7 and possibly also in the heating zone 8. A pump 15 (here a flexible-tube pump) can be used to supply the liquid back to the bioreactor vessel 3. The cooling medium surrounding the multiplicity of subducts 2' is temperature-controlled either directly in the cooling zone 7 for example using a Peltier element 13 or via a circulation pump 16 in a circuit 12 by means of a heat pump 14.

Example: Waste gas with a volume flow of 23 l/min of a 200 l bioreactor vessel 3 made of flexible plastic walls (Biostat Cultibag® STR200L, Sartorius Stedim Biotech GmbH) which is gassed from below with dry air and filled to two thirds with an aqueous culture medium, is supplied via the gas outflow duct 2 to the cooling zone 7 of the heat exchanger 6 in accordance with the FIGURE described above. The waste gas has a temperature of 34° C. and a relative humidity of 100%. This corresponds to a water load of about 35 g of water per kg of dry air or a specific water mass flow of 0.9 g/min. The waste gas is distributed over 50 subducts 2'. Each of the subducts is 50 cm long, has an internal diameter of 3 mm and a wall thickness of 0.7 mm. The material of the subducts is composed of polyurethane. The subducts 2' are surrounded by a flow of water as a cooling medium with a volume flow of 1 l/min and a temperature of 4° C. in counterflow. The waste gas flows in a laminar fashion at a rate of about 1 m/s through the subducts and is cooled in the process to a temperature of 6° C. at a relative humidity of 100%. This corresponds to a cooling efficiency of 44 W. The cooling medium, which has absorbed the removed heat, is pumped in the circuit 12 by way of the heat pump 14 (Frigomix® S, B. Braun Biotech International), cooled in said pump to 4° C. and subsequently recycled to the cooling zone 7 of the heat exchanger 6 of the waste gas system 1. The condensate (about 0.75 g/min) which forms during cooling is separated from the gas stream by guiding it through a condensate separator package of Raschig rings located in the base element 9. The precipitated liquid is guided from the base element 9 into the condensate collection vessel 11 and recycled from there into the bioreactor vessel 3 by means of a flexible-tube pump 15. The cooled waste gas is now furthermore supplied to the heating zone 8 of the heat exchanger 6. The heating zone 8 is formed by a pipe with a diameter of 6.5 cm, a length of 50 cm and a wall thickness of 3.0 mm. It is composed of a polyethylene terephthalate plastic. In said pipe, the waste gas flows at a rate of 0.1 m/s from bottom to top. Any remaining condensate drops cannot be entrained due to the low flow rate and flow back into the condensate collection vessel 11 via the base element 9. Heat supplied via the surroundings heats the waste gas and transfers any remaining small condensate drops to the gas phase. At the entry of the hydrophobic sterile filter 5, the waste gas has a temperature of 14° C. and a relative humidity of 59%. This corresponds to a heat efficiency of 3.5 W. Condensate which has collected in the condensate collection vessel 11 is recycled to the bioreactor vessel 3 via a flexible-tube pump 15. No blocking of the hydrophobic sterile filter could be ascertained over a time period of 67 hours.

REFERENCE LIST (1) waste gas system
(2) gas outflow duct
(2') subduct
(2") calming zone
(3) bioreactor vessel
(4) opening
(5) hydrophobic sterile filter
(6) heat exchanger
(7) cooling zone
(8) heating zone
(9) base element
(10) head element
(11) condensate collection vessel
(12) circuit
(13) Peltier element
(14) heat pump
(15) pump
(16) circulation pump

The invention claimed is:

1. Waste gas system (1) for bioreactors, comprising: at least one gas outflow duct (2) for discharging waste gas from a bioreactor vessel (3), a hydrophobic sterile filter (5) arranged upstream of an opening (4) of the at least one gas outflow duct (2) toward surroundings, a heat exchanger (6) located upstream of the hydrophobic sterile filter (5), the at least one gas outflow duct (2) being divided in at least one cooling zone (7) of the heat exchanger (6) into a multiplicity of subducts (2') and being extended in at least one heating zone (8) of the heat exchanger (6) to a calming zone (2") for the waste gas, the heating zone (8) and the calming zone (2') being configured to achieve a sufficiently low flow rate for impeding any remaining condensate drops from being entrained with the waste gas and transported to the hydrophobic sterile filter (5).

2. Waste gas system according to claim 1, wherein the cooling and the heating zones (7, 8) of the heat exchanger (6) are connected in series and arranged in mutually parallel fashion.

3. Waste gas system according to claim 2, wherein the cooling and the heating zones (7, 8) of the heat exchanger (6) are interconnected in a communicating fashion via a base element (9).

4. Waste gas system according to claim 3, wherein the cooling and the heating zones (7, 8) of the heat exchanger (6) are held together via a head element (10).

5. Waste gas system according to claim 2, wherein the cooling and the heating zones (7, 8) of the heat exchanger (6) are arranged such that they are spaced apart from each other.

6. Waste gas system according to claim 1, wherein a condensate separator package is integrated in the gas outflow duct (2) downstream of the cooling zones (7) of the heat exchanger (6).

7. Waste gas system according to claim 6, wherein the condensate separator package is arranged in a base element (9) that interconnects the heating and cooling zones (7, 8) and that communicates with the heating and cooling zones (7, 8).

8. Waste gas system according to claim 7, wherein the condensate separator package includes a non-woven or fill bodies.

9. Waste gas system according to claim 1, wherein the multiplicity of subducts (2') is surrounded by a cooling medium.

10. Waste gas system according to claim 9, wherein at least one Peltier element (13) is introduced into the cooling medium for cooling.

11. Waste gas system according to claim 9, wherein heat can be removed from the cooling medium in a circuit (12).

12. Waste gas system according to claim 11, wherein the circuit is connected to a heat pump (14) for the removal of the heat.

13. Waste gas system according to claim 12, wherein the heat pump (14) is a compressor heat pump.

14. Waste gas system according to claim 1, wherein the hydrophobic sterile filter (5) is integrated in the exit of the heating zone (8) of the heat exchanger (6).

15. Waste gas system according to claim 1, wherein the waste gas system (1) is made of plastic.

16. Waste gas system according to claim 15, wherein the waste gas system (1) is operable with a bioreactor vessel (3) composed of flexible plastic.

17. Waste gas system according to claim 1, wherein the subducts (2') are composed of polyurethane, silicone or polyalkylene.

18. Waste gas system according to claim 17, wherein subducts (2') are flexible tubes.

19. Waste gas system according to claim 18, wherein the wall thickness of the subducts (2') or of the flexible tubes is less than 2 mm.

20. Waste gas system according to claim 1, wherein the waste gas during flowing through the multiplicity of subducts (2') has a laminar flow.

21. A waste gas system for bioreactors, comprising: a bioreactor vessel (3), at least one gas outflow duct (2) for discharging waste gas from the bioreactor vessel (3), a hydrophobic sterile filter (5) arranged upstream of an opening (4) of the at least one gas outflow duct (2) toward surroundings, a heat exchanger (6) located upstream of the hydrophobic sterile filter (5), the at least one gas outflow duct (2) being divided in at least one cooling zone (7) of the heat exchanger (6) into a multiplicity of subducts (2') and is extended in at least one heating zone (8) of the heat exchanger (6) to a calming zone (2") for the waste gas, the cooling and the heating zones (7, 8) of the heat exchanger (6) being interconnected in a communicating fashion via a base element (9), wherein at least the cooling zone (7) of the heat exchanger (6) is connected in a communicating fashion to a condensate collection vessel (11) via the base element (9), the condensate collection vessel (11) being underneath the heat exchanger (6) and upstream of the hydrophobic sterile filter (5).

22. A waste gas system for bioreactors, comprising: at least one gas outflow duct (2) for discharging waste gas from a bioreactor vessel (3), a hydrophobic sterile filter (5) arranged upstream of an opening (4) of the at least one gas outflow duct (2) toward surroundings, a heat exchanger (6) located upstream of the hydrophobic sterile filter (5), the at least one gas outflow duct (2) being divided in at least one cooling zone (7) of the heat exchanger (6) into a multiplicity of subducts (2') and is extended in at least one heating zone (8) of the heat exchanger (6) to a calming zone (2") for the waste gas, wherein the cooling zone (7) of the heating exchanger (6) is connected in a communicating fashion to a condensate collection vessel (11) that is connected to the bioreactor vessel (3) and/or to the at least one heating zone (8) of the heat exchanger (6).

* * * * *